United States Patent [19]
Von Berg

[11] Patent Number: 5,406,958
[45] Date of Patent: Apr. 18, 1995

[54] MEDICO-SURGICAL SENSOR ASSEMBLIES
[75] Inventor: Peter Von Berg, Tiburon, Calif.
[73] Assignee: Smiths Industries Public Limited Company, London, England
[21] Appl. No.: 112,518
[22] Filed: Aug. 27, 1993
[30] Foreign Application Priority Data Sep. 19, 1992 [GB] United Kingdom ................. 9219943

[51] Int. Cl.6 .............................................. A61B 5/00
[52] U.S. Cl. .................................................. 128/748
[58] Field of Search ................ 128/748, 642, 774, 782
[56] References Cited

U.S. PATENT DOCUMENTS

| | | | |
|---|---|---|---|
| 3,649,948 | 3/1972 | Porter | 128/748 |
| 3,686,958 | 8/1972 | Porter et al. | 128/748 |
| 4,114,603 | 9/1978 | Wilkinson | 128/748 |
| 4,246,908 | 1/1981 | Inagaki et al. | 128/748 |
| 5,054,497 | 10/1991 | Kapp et al. | 128/748 |
| 5,117,836 | 6/1992 | Millar | 128/748 |

Primary Examiner—Max Hindenburg
Attorney, Agent, or Firm—Pollock, VandeSande and Priddy

[57] ABSTRACT

An intercranial pressure sensor assembly has a sensor at one end of an electrical cable. At its other end, the cable has a low profile coupling with annular contact members spaced axially along its length. A guide of a plastics material has an attachment with a tapering surface at one end from which extends a flexible lead. The guide is screwed to the coupling by means of an internal thread on the attachment and is used to pull the cable beneath tissue on the scalp. After the sensor is correctly positioned, the guide is removed and the coupling can be connected to a monitor.

8 Claims, 2 Drawing Sheets

5,406,958

MEDICO-SURGICAL SENSOR ASSEMBLIES

This invention relates to medico-surgical sensor assemblies.

BACKGROUND OF THE INVENTION

The invention is more particularly but not exclusively concerned with intercranial pressure sensor assemblies.

Intercranial pressure sensor assemblies conventionally comprise an electrical pressure sensor or transducer connected by an electrical cable to an electrical coupling. The coupling is of a conventional kind and is connected, in use, to a mating coupling, which is in turn connected to an electrical cable extending to electrical monitoring apparatus that records or displays the pressure value. The assembly is installed in the patient in the following way. A hole is drilled through the bone of the skull and two spaced incisions are made with a scalpel, or similar instrument, to form a tunnel through the skin and subcutaneous tissue on the scalp close to the hole. The nose of a pair of forceps is pushed into one incision so that it extends along the tunnel and emerges through the second incision. The nose of the forceps is opened, the sensor is inserted between them and the forceps are closed to grip the sensor tightly. Next, the forceps are pulled rearwardly back through the tunnel and out of the first incision, taking the sensor with them. The sensor is then pushed through the hole into the head so that it lies between the dura and the skull bone, with the pressure-sensitive side of the sensor facing inwards. The sensor is thereby located in the skull, with its cable extending out of the second incision.

The problem with this technique is that the pressure sensor is relatively delicate and is often damaged by the forceps. This can lead to failure or to erroneous readings of pressure.

BRIEF SUMMARY OF THE INVENTION

It is an object of the present invention to provide a sensor assembly that can be located easily with a reduced risk of damage.

According to one aspect of the present invention there is provided a medico-surgical sensor assembly comprising a sensor, a cable connected to the sensor at one end and to a coupling at its other end, and guide means comprising a flexible lead having attachment means at one end adapted for releasably attaching the guide means to the coupling, the attachment means and coupling when attached providing a tapering external surface such that the assembly can be gripped by the lead and pulled through an incision tunnelled through tissue to locate the sensor with the coupling and cable extending through the incision.

The sensor is preferably an electrical sensor, the cable an electrical cable and the coupling an electrical coupling. The coupling may have a plurality of contact members spaced from one another along the coupling. The contact members may be of annular shape and arranged axially of one another. The sensor is preferably a pressure sensor. The attachment means and the coupling preferably have cooperating screw threads, the attachment means having an internal screw thread and the coupling having an external screw thread. The lead and attachment means may be of a plastics material.

An electrical intercranial pressure sensor assembly and its method of location in accordance with the present invention, will now be described, by way of example, with reference to the accompanying drawings.

DETAILED DESCRIPTION OF THE PREFERRED EMBODIMENT

Figure 1:
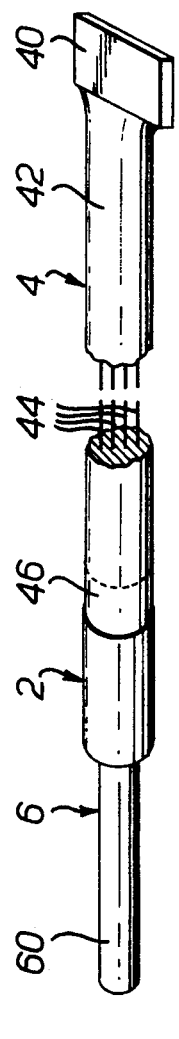
FIG. 1 is a perspective view of the assembly.
Figure 2:
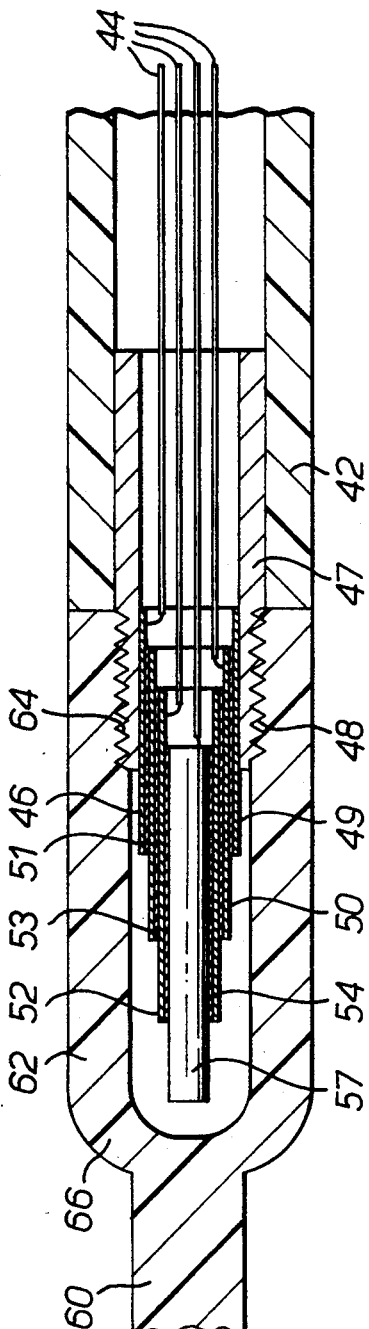
FIG. 2 is a sectional elevation view of a part of the assembly.

With reference to FIGS. 1 and 2, the intercranial pressure sensor assembly 2 comprises a patient assembly 4 to the rear end of which is attached a guide 6.

The patient assembly 4 comprises, at its right-hand end, a conventional electrical pressure sensor 40 to which is connected an electrical cable 42, which is typically about 100 mm long. Four wires 44 within the cable 42 extend to its left-hand end where they are connected to a low profile electrical coupling 46. The coupling 46 is designed to have as small a cross section as possible, for reasons that will become apparent later.

The coupling 46 is joined to the cable 42 by an insulating cylindrical sleeve 47 of circular section with an external diameter of about 4mm and an external screw thread 48. A cylindrical metal shell 49 projects from the rear of the sleeve 47 to provide a first annular contact where the shell is exposed at the end of the insulating sleeve. One of the wires 44 is soldered, or otherwise connected to the shell 49 at its forward end. A second metal shell 50 extends coaxially within the first shell 49 and projects from it by a short distance to provide a second annular contact, the two shells being insulated from one another where they overlap by an insulating cuff 51 between the two shells. The second shell 50 is connected to another one of the wires 44 at its forward end. A third annular contact of the coupling 46 is provided by a third metal shell 52 projecting from the rear end of the second shell 50 and being insulated from it by a second insulating cuff 53. A third of the wires 44 is connected to the forward end of this third shell 52. The fourth contact of the coupling 46 is provided by a coaxial metal rod 57 projecting from the rear end of the third shell 52 and insulated from it by a third insulating cuff 54. The fourth of the wires 4 is connected to the forward end of the rod 47. Because the four contacts 49, 50, 52 and 57 are spaced axially, along the length of the coupling, the diameter of the coupling is kept to a minimum.

The guide 6 can take several different forms. In general, it comprises a flexible lead with an attachment 62, which can be attached to the coupling 46 on the patient assembly. In the example illustrated, the lead takes the form of a length of solid, flexible plastics cord 60 about 50 mm long. Alternatively, a length of hollow plastic tube could be used. The attachment 62 on the guide 6 is a cylindrical plastics sleeve with an internal screw thread 64 that is engageable with the thread 48 on the sleeve 47. The right-hand end of the attachment 62 is open so that it can be secured on the patient assembly 4; the left-hand end of the attachment 62 has a taper 66. The guide 6 is used solely for location of the patient assembly 4 and does not serve any electrical function.

Figure 3:
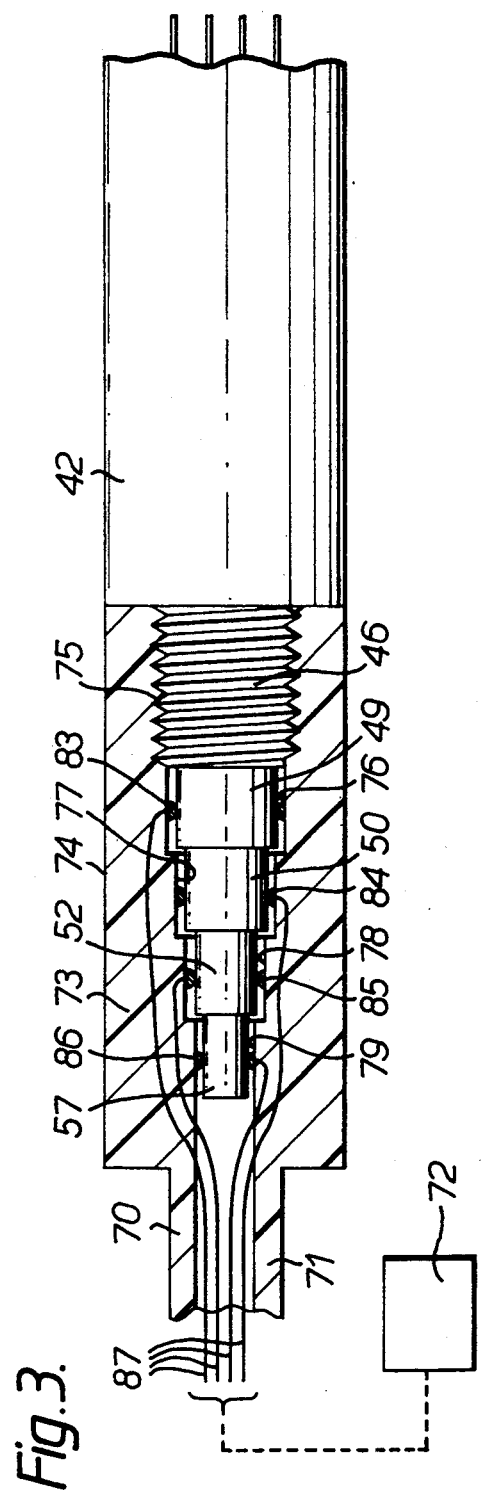
FIG. 3 is a sectional elevation view of a part of the assembly coupled to monitoring equipment.

After installation of the pressure sensor 40, in the manner described below, the guide 6 is removed and disposed of. Electrical connection to the coupling 46 is made by an equipment lead 70, as shown in FIG. 3. The lead 70 includes a cable 71 that extends from pressure monitoring equipment 72 at one end to a coupling 73 at the other end. The equipment coupling 73 has an outer insulating shell 74 with an internal screw thread 75 formed around its forward end. Internally, the shell 74 has four steps 76 to 79 of progressively smaller diameters which correspond to the four contact regions 49, 50, 52 and 57 of the patient coupling 46. Each of the steps 76 to 79 has a respective electrical contact 83 to 86 connected to respective ones of four wires 87 in the cable 71. When the equipment coupling 73 is screwed onto the patient coupling 46, the contacts 83 to 86 in the equipment coupling connect with the contact regions 49, 50, 52 and 57 in the patient coupling so that the sensor 40 is electrically connected to the monitoring equipment 72.

The pressure sensor assembly 2 is installed in the manner described below with reference to FIGS. 4 to 7.

Figure 4:
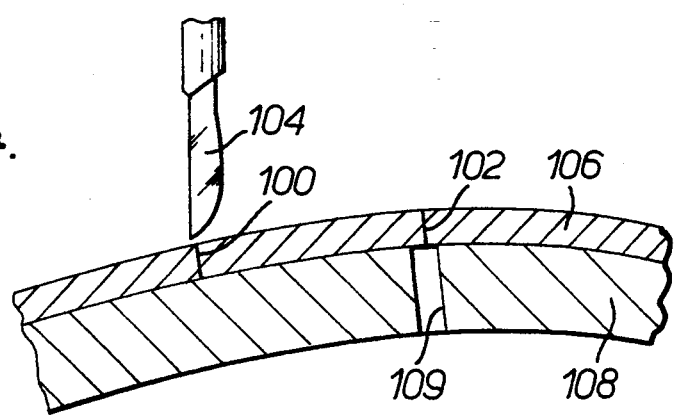
FIGS. 4 to 7 illustrate the method of use.
Figure 5:
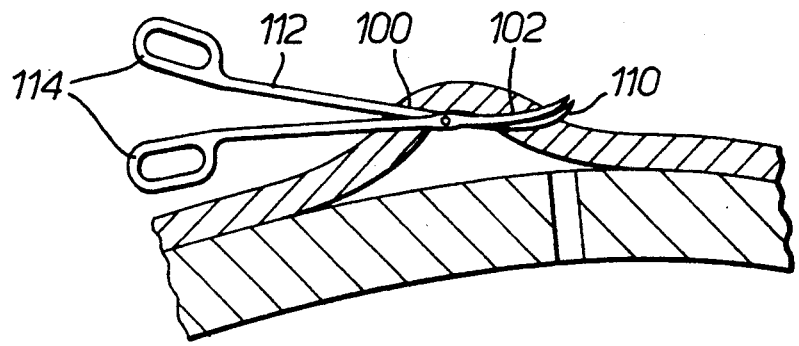
Figure 6:
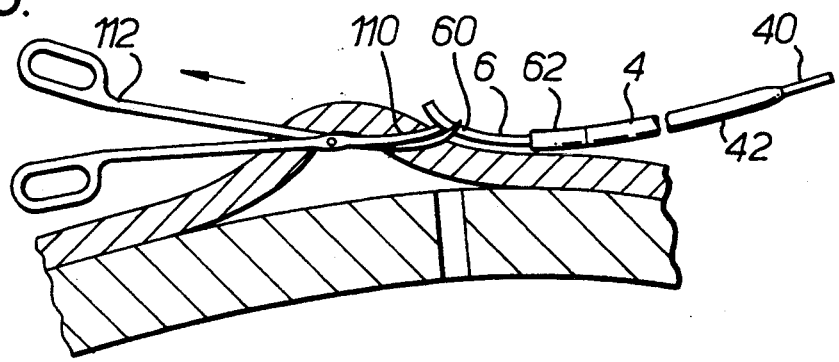
Figure 7:
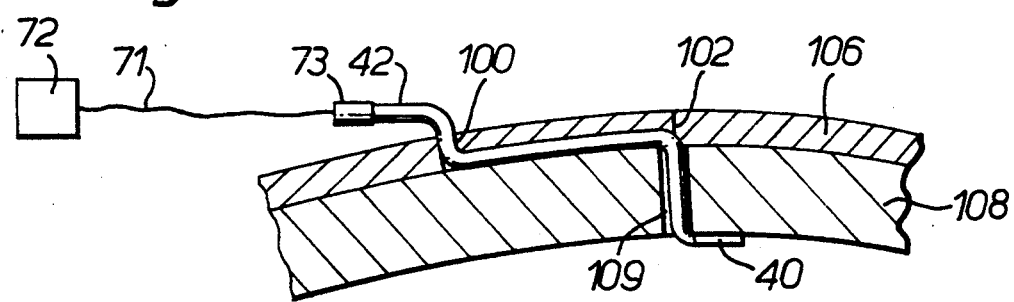

First, as shown in FIG. 4 two parallel incisions 100 and 102 are made with a scalpel 104 through the skin and subcutaneous tissue 106 overlying the skull 108. The incisions 100 and 102 are each about 20 mm long and are spaced from each other by about 40 mm. A hole 109 is drilled through the bone of the skull 108 beneath the second incision 102. The next step, as shown in FIG. 5, is to insert the curved nose 110 of a pair of forceps 112 through the first incision 100, push it beneath the skin and subcutaneous tissue 106 and angle it upwardly so that it emerges through the second incision 102 by a short distance. The handles 114 of the forceps 112 are then separated so that the nose 110 also opens by a short distance. The left-hand end of the lead 60 on the guide means 6 is placed between the jaws of the nose 110 and the forceps 112 are closed so that the guide means 6 is gripped firmly, as shown in FIG. 6. Next, the forceps 112 are pulled back, taking the lead 60 of the guide means 6 through the incision 102 and beneath the skin 106. The taper 66 and the small cross-section of the attachment 62 and the coupling 46 enable them to be pulled through the incision without difficulty. As the forceps 112 are pulled further back, the guide means 6 emerges through the first incision 100 while the cable 42 is pulled through the second incision 102 until the pressure sensor 40 comes close to the second incision 102. The forceps 112 are then released and the pressure sensor 40 is pushed through the incision into the hole 109 until the sensor lies just inside the skull, between the bone of the skull and the dura, with the pressure-sensitive side of the sensor facing inwardly. The guide 6 is then unscrewed from the patient coupling 46 and replaced by the electrical coupling 73 so that the sensor 40 is electrically connected to the patient monitor 72 as shown in FIG. 7.

It can be seen that, by this technique, there is no need to grip the pressure sensor 40, thereby avoiding the risk of damage to the sensor.

It will be appreciated that the assemblies could have an alternative sensor such as, for example, a temperature sensor, chemical sensor, blood oxygen sensor of the like. The sensor and cable need not be electrical but could be optical, in which case the coupling would be an optical coupling.

What I claim is:

1. A medico-surgical sensor assembly comprising: an electrical pressure sensor; an electrical coupling; an electrical cable having a first end and a second end; means connecting the cable to the sensor at said first end; means connecting the cable to the coupling at said second end; and a flexible guide lead separate from the cable having an attachment at one end that is releasably attachable to the coupling, the attachment and coupling when attached providing a tapering external surface such that the assembly can be gripped by the guide lead and pulled through an incision tunneled through tissue to locate the sensor with the coupling and cable extending through the incision.

2. An assembly according to claim 1, wherein the coupling has a plurality of electrical contact members spaced from one another along the coupling.

3. An assembly according to claim 2, wherein the contact members are of annular shape, the contact members being arranged axially of one another.

4. An assembly according to claim 1, wherein the attachment and the coupling have cooperating screw threads.

5. An assembly according to claim 4, wherein the attachment has an internal screw thread and the coupling has an external screw thread.

6. An assembly according to claim 1, wherein the lead and attachment are of a plastics material.

7. An intercranial pressure sensor assembly comprising: an electrical pressure sensor; an electrical coupling; an electrical cable having a first end and a second end; means connecting said cable to said sensor at said first end; means connecting said cable to said coupling at said second end; and a flexible guide lead separate from the cable having an attachment at one end that is releasably attachable to said coupling, the attachment and coupling when attached to one another providing a tapering external surface such that the assembly can be gripped by said guide lead and pulled through an incision tunneled through and below the skin and subcutaneous tissue overlying the skull of a patient to locate the sensor and a portion of the cable below the patient's said skin and subcutaneous tissue with the coupling and cable extending through the incision to the exterior of the patient's said skin and tissue.

8. A method of locating a sensor of a sensor assembly in tissue of a patient comprising the steps of: providing a sensor assembly having a sensor at one end, a coupling at the other end and a cable interconnecting the sensor and coupling; attaching a flexible guide lead to the coupling; pushing gripping means through tissue to tunnel below the tissue of a patient and emerge from one side of the tissue; gripping the end of the guide lead remote from the coupling with the gripping means; pulling the gripping means back through and below the tissue together with the flexible guide lead to position the sensor and a portion of the cable below the tissue and adjacent a desired location in the patient; releasing the gripping means; detaching the guide lead; and connecting the cable to monitoring equipment.

* * * * *